(12) United States Patent
Hsieh

(10) Patent No.: US 6,233,308 B1
(45) Date of Patent: *May 15, 2001

(54) METHODS AND APPARATUS FOR ARTIFACT COMPENSATION WITH VARIABLE ANGULAR SAMPLING

(75) Inventor: Jiang Hsieh, Brookfield, WI (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/272,708

(22) Filed: Mar. 19, 1999

(51) Int. Cl.⁷ .................................................. A61B 6/03
(52) U.S. Cl. .................... 378/62; 378/4; 378/8; 378/19; 378/901
(58) Field of Search ................ 378/4, 8, 19, 901, 378/62

(56) References Cited

U.S. PATENT DOCUMENTS

| 5,228,070 | 7/1993 | Mattson | 378/19 |
| 5,668,845 | 9/1997 | Miguta | 378/4 |
| 5,828,718 | * 10/1998 | Ruth et al. | 378/19 |
| 5,848,117 | * 12/1998 | Urchuk et al. | 378/19 |

FOREIGN PATENT DOCUMENTS

| 0 119 664 | 9/1984 | (EP) | A61B/6/02 |

* cited by examiner

Primary Examiner—David V. Bruce
(74) Attorney, Agent, or Firm—Armstrong Teasdale LLP; Christian G. Cabou

(57) ABSTRACT

The present invention, in one form, includes an imaging system having a x-ray source and a digital detector array. The system alters an angular spacing between samples of projection data as a function of the projection angle so that aliasing artifacts are reduced. More specifically and in one embodiment, after identifying at least two projection angle regions, a first view sampling rate is utilized to collect projection data for the first region. As the projection angle becomes equal to the second region, the view sampling rate is altered to a second view sampling rate. A complete volumetric image of an object is then generated from the data.

31 Claims, 2 Drawing Sheets

METHODS AND APPARATUS FOR ARTIFACT COMPENSATION WITH VARIABLE ANGULAR SAMPLING

BACKGROUND OF THE INVENTION

This invention relates generally to an imaging system, and more particularly, to artifact compensation with variable angular sampling for generating volumetric images of an object.

In at least one known imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location.

In at least one known type of imaging system, commonly known as a computed tomography (CT) system, a group of x-ray attenuation measurements, i.e., projection data, from the detector array is referred to as a "view". A "scan" of the object comprises a set of views made at different projection angles, or view angles, during at least one revolution of the x-ray source and detector. In an axial scan, the projection data is processed to construct an image that corresponds to a two dimensional slice taken through the object. Typically, each slice represents less than approximately 2 cm of coverage of the patient in the patient or z-axis and is generated from data collected from 984 views during a rotation of the gantry. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT system collects data utilizing a large flat panel digital x-ray device, or detector, having a plurality of pixels arranged in rows and columns. However, such flat panels suffer from slow read-out times thereby increasing the time required to generate the image. For at least one known CT system the large flat panel is capable of collecting only 33 views per second. Utilizing a 10 second scan, only 330 views are collected, resulting in a significant reduction in the number of views collected per rotation of the gantry versus other known imaging systems. As is known in the art, such view under-sampling causes aliasing artifacts. The aliasing artifacts are the most severe in the upper peripheral of the patient as largely caused by the sharp structures of the high density elements, such as a spine. In addition, as a result of the spine orientation, the worst streaking artifact is parallel to the patient y-axis, indicating the most severe under-sampling occurs when the x-ray source is substantially aligned with the patient Y-axis.

It is desirable to provide an imaging system which generates a volumetric image of a complete object within a patient utilizing data collected from a single rotation of the gantry. It would also be desirable to provide such a system which alters the view collection rate as a function of projection angle so that aliasing artifacts are reduced and the scan is completed in a reasonable period of time.

BRIEF SUMMARY OF THE INVENTION

These and other objects may be attained by a digital imaging system which, in one embodiment, alters an angular spacing between samples of projection data so that image aliasing artifacts are reduced. Particularly and in one embodiment, the imaging system includes a rotatable gantry having an x-ray source that projects an x-ray beam toward a digital detector array. The digital detector array is fabricated in a panel configuration having a plurality of pixels arranged in rows and columns. The digital detector array is configured so that a volumetric image is generated for an entire object within a patient by rotating the gantry up to one complete rotation.

In operation, prior to performing a scan on a patient, at least two projection angle regions are identified with respect to the object. As the gantry is rotated through a plurality of projection angles, the angular spacing at which the projection data is collected from each region is altered. More specifically, a view sampling rate for each region is altered so that the time required to complete the scan is minimized and aliasing artifacts are reduced. Alternatively, the rotational speed of the x-ray source is decreased in areas containing sharp structures of high density objects so that the view sampling rate is increased to reduce aliasing artifacts. For those areas not containing such sharp structures, the rotational speed of the gantry is increased so that the view sampling rate is decreased.

After collecting the data utilizing the different view sampling rates, the projection data representing the collected views is interpolated to generate an additional number of views. The views are then reconstructed with known reconstruction algorithms to generate the volumetric image.

The above described system generates a volumetric tomographic image of a complete object within a patient utilizing data collected from a single rotation of the gantry. In addition, aliasing artifacts are reduced by altering the view sampling rate as a function of the projection angle. Particularly, by collecting a higher rate of views in certain regions and a lower rate of views in other regions, scan time is reduced and aliasing artifacts are reduced.

DETAILED DESCRIPTION OF THE INVENTION

Figure 1:
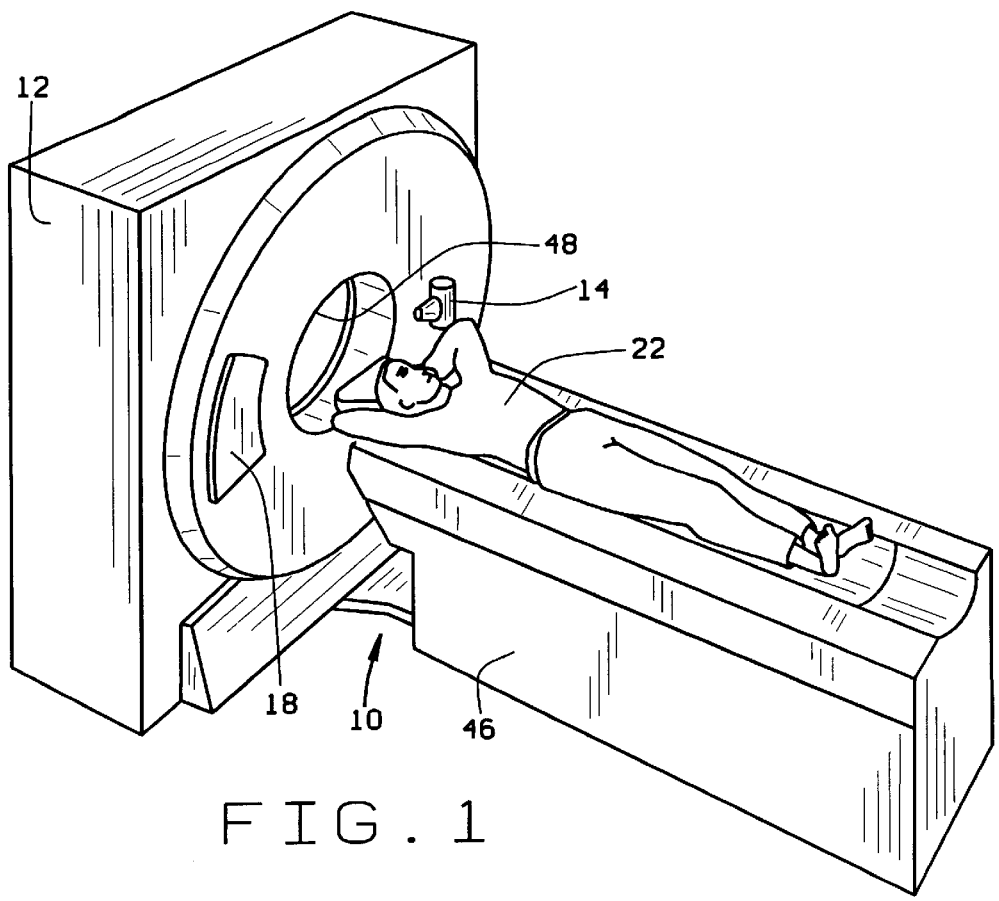
FIG. 1 is a pictorial view of a CT imaging system.
Figure 2:
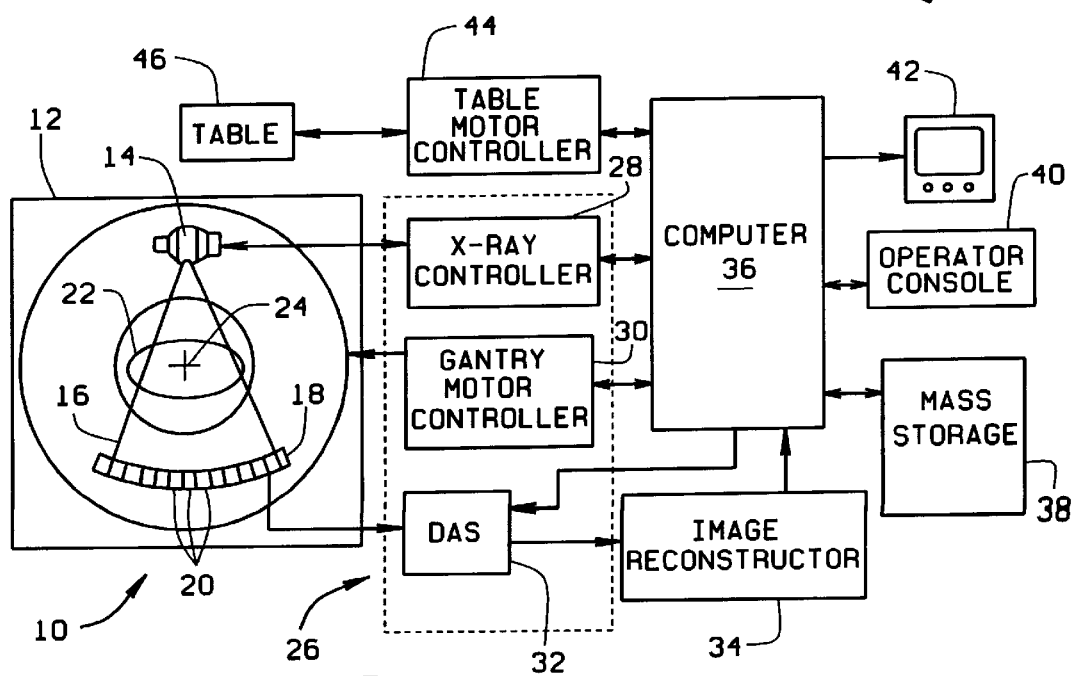
FIG. 2 is a block schematic diagram of the system illustrated in FIG. 1.

Referring to FIGS. 1 and 2, a computed tomograph (CT) imaging system 10 is shown as including a rotatable gantry 12 representative of a "third generation" CT scanner. In one embodiment, an x-ray source 14 is coupled to gantry 12 and projects an x-ray beam 16 toward a digital detector array 18 on the opposite side of gantry 12. In one embodiment, detector array 18 is fabricated in a panel configuration having a plurality of pixels (not shown) arranged in rows and columns. Each pixel includes a photosensor, such as a photodiode, that is coupled via a switching transistor to two separate address lines, a scan line and a data line. The radiation incident on a scintillator material (not shown) and the pixel photosensors measure, by way of change in the charge across the photodiode, the amount of light generated by x-ray interaction with the scintillator. As a result, each pixel produces a digital electrical signal that represents the intensity, after attenuation of patient 22, of an impinging x-ray beam 16. Detector array 18 is sized so that a volumetric image is generated for an entire object, or organ, within patient 22, i.e., a heart (not shown). In various embodiment, detector array 18 is approximately 40 cm wide (x-axis) by 20 to 40 cm in height (z-axis) and is configured to produce projection data at a rate of up to 40 frames per second. Of course, in other embodiments, the size of detector array 18 may be altered for the specific system requirements.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. In one embodiment, DAS 32 includes a plurality of channels and is referred to as a multiple channel DAS.

An image reconstructor 34 receives sampled digital x-ray projection data from DAS 32 and performs high speed image reconstruction. The reconstructed image is applied as an input to a computer 36 which stores the image in a mass storage device 38. Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48 to properly position patient 22.

Figure 3:
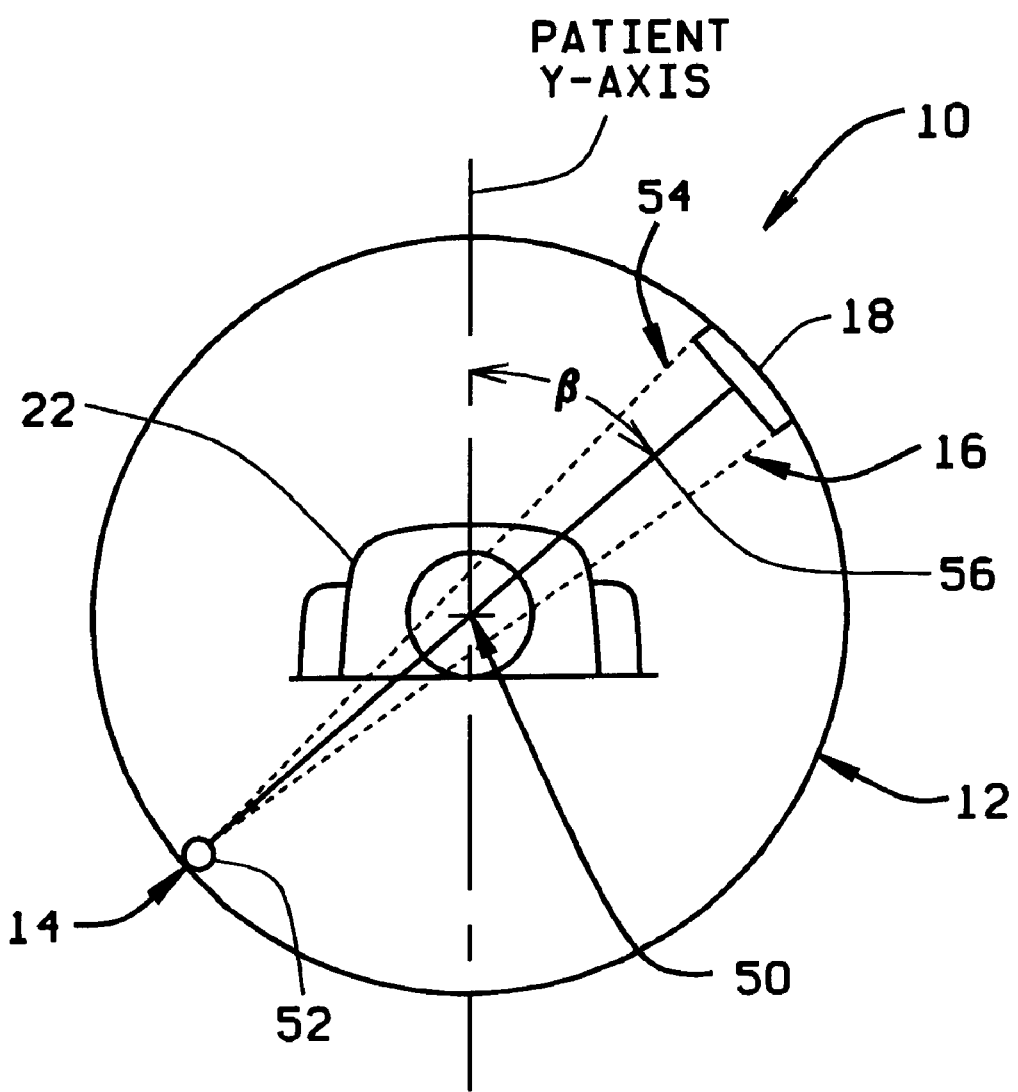
FIG. 3 is a schematic illustration of the gantry of the system illustrated in FIG. 1.

FIG. 3 is schematic illustration of gantry 12, x-ray source 14, detector array 18 and patient 22. Gantry 12 and the components mounted thereon rotate about a center of rotation 50. X-ray source 14 emits x-ray beam 16 from a focal spot 52 of source 14. X-ray beam 16 is collimated by a pre-patient collimator (not shown) and a collimated beam 54 is projected toward detector array 18 along a fan beam axis 56 centered within beam 16. As shown in FIG. 3, fan beam axis 56 is at a projection angle, $\beta$, with respect to a Y-axis of patient 22. During a scan of patient 22, as gantry 12 is rotated, x-ray beam 16 is emitted from source 14 and projection data is collected by detector array 18 from a plurality of projection angles, $\beta$. In one embodiment, the projection data is utilized to generate an image of the object by rotating gantry 12 up to one complete rotation, i.e., projection data is collected for values of $\beta$ from 0 degrees up to 360 degrees. In other embodiments, projection data is collected during multiple rotations of gantry 12. For example, as known in the art, the projection data is collected during a helical scan or a CINE CT scan.

The architecture of system 10 described above provides many important advantages, including that system 10 may be configured so that a volumetric image of an entire object (not shown) within patient 22 is generated by collecting a limited number of samples, or views of projection data. By altering an angular spacing between the samples as a function of the projection angle, system 10 minimizes scan time while reducing aliasing artifacts caused by the limited response time of detector array 18.

More specifically, as gantry 12 is rotated through a series of projection angles, an angular spacing is altered by modifying the amount of change in the projection angle, $\Delta\beta$, between each view. Particularly and in one embodiment, as projection data samples are collected, the angular spacing between each sample is altered by altering, or adjusting, a rotational speed of gantry 12 using gantry motor controller 30. As gantry 12 is rotated, control mechanism 26 of system 10 alters the signals supplied to gantry motor controller 30 so that the rotational speed of gantry 12 is altered as a function of the projection angle. Utilizing a constant DAS sampling frequency to measure the signals supplied by detector array 18, the changing rotational speed of gantry 12 alters the $\Delta\beta$ between views. More specifically, by altering the rotational speed of x-ray 14 as a function of the projection angle, the $\Delta\beta$ between views for selected, or identified region are larger or smaller than the $\Delta\beta$ between views of other selected, or identified regions.

In one embodiment, a first projection angle range, or region, and at least a second projection angle range, or region, are identified. More specifically and in one embodiment, where an axis of a sharp structure of a high density element, such as a spine, is determined to be substantially parallel with the Y-axis of patient 22, a center of a first projection angle region is then identified as being approximately aligned along the sharp structure axis, i.e., the Y-axis. In one embodiment, the center of the first projection angle range, $C_{FPAR}$, equals 0 degrees, and a center of the second projection angle range, $C_{SPAR}$, is also aligned along the sharp structure axis and is equal to 180 degrees, i.e., $C_{SPAR}$ equal $C_{FPAR}$ +180 degrees. After identifying the first and second projection angle regions, a third projection angle range is then identified as an area outside the first projection angle range and the second projection angle range. In other embodiments, any number of regions may be identified and the view sampling rate for each region, or range, may be altered.

After identifying the regions, as described above, a first and second projection angle regions aligned along the sharp structure axis and a third region, gantry 12 is rotated through a series of projection angles. More specifically and in one embodiment, as gantry 12 is rotated within the first projection angle region and the second projection angle region, a first gantry rotation speed is utilized so that a selected number of views are collected from each region. As gantry 12 continues to rotate and the projection angle is no longer contained within the first or second projection angle region and enters the third projection angle region, the rotational speed of gantry 12 is altered to a second rotational speed, wherein the second speed is not equal to the first rotational speed. In one embodiment having three projection angle regions, the second rotational speed for the third region is altered so that the $\Delta\beta$ between each view is increased. More specifically, system 10 reduces aliasing artifacts by increasing the view sampling rate when $\beta$ is within the first or second projection angle region and decreases the view sampling rate to a second view sampling rate for the third projection region.

In another embodiment, the rotational speed of gantry 12 is continuously changed, or altered, as a function of the projection angle. For example and in one embodiment, the gantry rotational speed is continuously altered as a function of projection angle so that the rotational speed is a minimum at the $C_{FPAR}$ and $C_{SPAR}$ and a maximum rotational speed at the center of the third region.

For example, where the center of the first and second projection angle ranges are identified as $\beta$ equal to 0 and 180 degrees, respectively, detector array 18 generates 33 views per second and a ten second scan is utilized, up to 330 views may be generated during a complete rotation of gantry 12. Using a range of 30 degrees on each side of the first and second projection angle region centers, the first range equals −30 degrees to +30 degrees and the second range equals 150 degrees to 210 degrees. The third projection angle range is defined as the areas located outside of the first region and the second region, i.e., 30 degrees≦β≦150 degrees and 210 degrees≦β≦330 degrees.

Using a scan starting angle of 0 degrees, gantry 12 is rotated so that the first view sampling rate is 328 views per rotation until β equals 30 degrees. As β becomes greater than 30 degrees, exceeding the first projection angle range, the speed of gantry 12 is increased to a third view sampling rate of 247 views per rotation for the projection angle range of greater than 30 degrees and less than 150 degrees. For the second projection range of 150 degrees to 210 degrees, the speed of gantry 12 is decreased so that the second view sampling rate is 328 views per rotation. For projection angles of greater than 210 degrees to less than 330 degrees, the speed of gantry 12 is increased so that the third view sampling rate of 247 views per rotation is utilized. As β becomes equal to 330 degrees, the rotational speed of gantry 12 is decreased so that the projection data is collected at the first view sampling rate of 328 views per rotation. Upon completion of the rotation by gantry 12, 274 views of projection data have been collected.

In another embodiment, the view sampling rate is altered by altering, or adjusting, the sampling frequency of detector array 18. More specifically, as gantry 12 is rotated, a sampling frequency of DAS 32 is altered as a function of the projection angle. As a result of changing the sampling frequency of DAS 32, the Δβ between views for certain regions are greater or less than the Δβ for other regions. Particularly, to increase the view sampling rate, the DAS sampling frequency is increased. To decrease the view sampling rate, the DAS sampling frequency is reduced.

In another embodiment utilizing a weighting function to minimize motion of patient 22, the number of views required to be collected to generate the image may be further reduced. The weighting function, in one embodiment, has the characteristics that it reduces the contribution of the projection data collected near a beginning and an end of a scan to near zero and increases the contribution of the conjugate projection data. Specifically and in one embodiment, the weight applied to the projection data collected from the beginning and the end of the scan is approximately zero, the weight applied to the middle of the scan is approximately two, and the weight applied to the remaining projection data is approximately equal to one. In other embodiments, the weights applied to the projection data may be altered in accordance with methods known in the art.

As a result of the limited contribution of beginning and end projection data to the final image, the view sampling rate for the beginning and the end of a scan may be reduced without increasing aliasing artifacts. Particularly, by identifying the first projection angle region as being near the beginning and the end of the scan and a second projection angle as including the remaining projection angles, the sampling rate for the first projection angle region may be decreased without increasing aliasing artifacts. Therefore, if the number of views collected remain constant, the time required to complete the scan may be reduced. Alternatively, if the scan time remains constant, the view sampling rate may be increased for the second projection angle region to improve image quality.

For example, utilizing a starting angle of 90 degrees, a center of the first projection angle range of 90 degrees and a first projection angle region of 60 degrees, a lower first sampling rate is used only for a first projection angle region of 60 degrees to 120 degrees. As a result, the projection data may be collected in the first projection angle region at a sampling rate of 328 views per gantry rotation, while the projection data for the second projection angle region, is collected at a view sampling rate of 492 views per rotation.

Utilizing the collected projection data, system 10 generates the image using known reconstruction algorithms. More specifically, upon completion of a scan, the projection data collected by detector array 18 includes a number of total views having at least two different view sampling rates. In one embodiment, the total number of views may be increased with known interpolation algorithms so that the angular increment, Δβ, in the resulting projections will be uniform. For example, projection data samples having angular spacings of 328 and 492 views/rotation will be interpolated to 984 views/rotation.

In another embodiment, the collected projection data is interpolated to ensure smoother view to view transitions. More specifically, the collected views in a transition position are determined by interpolation with the next view. In other embodiments, linear interpolation, higher order interpolation, or zero padding in the frequency domain may be used to increase the number of views to the desired number so that known reconstruction algorithms may be used.

In another embodiment, the view sampling rate or angular spacing, is continuously altered, or varied, as a function of the projection angle. More specifically, the view sampling rate is continuously altered so that the number of views collected may be further reduced. For example, using the above described example where the sharp structure axis is substantially parallel to the patient Y-axis, as the projection angle nears 360 degrees, the view sampling rate is continuously increased to a maximum value when the projection angle equals 360 degrees. As the projection angle becomes greater than 360, or 0, degrees, the view sampling rate is continuously decreased until projection angle becomes equal to 90 degrees. Specifically and in one embodiment, for the range of 0 degrees to 90 degrees the speed of gantry 12 is continuously increased so that a maximum speed occurs at 90 degrees. Once the projection angle becomes greater than 90 degrees, the speed of gantry 12 is continuously decreased to a minimum value when the projection angle equals 180 degrees. As gantry 12 is rotated from 180 degrees to 270 degrees, the gantry speed is increased to a maximum speed occurring at 270 degrees. From 270 degrees to 360 degrees, the gantry speed is decreased to a minimum speed at 360 degrees.

In another embodiment, the view sampling rate may be adjusted based on a patient size or Region Of Interest (ROI) size. For example, where the ROI is small, the view sampling rate may be decreased. In addition, the lose of spatial resolution, as a result of the reduced angular sampling, may be at least partially compensated for by modifying a frequency response of a convolution kernel used in the reconstruction algorithm.

The above described system generates a volumetric image of a complete object within a patient utilizing data collected from a single rotation of the gantry. In addition, aliasing artifacts are reduced by altering the view sampling rate as a function of the projection angle. Particularly, by collecting a higher rate of views in certain regions and a lower rate of views in other regions, aliasing artifacts are reduced.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, in an alternative embodiment, the imaging system 10 configured as a "fourth generation" system having a rotating x-ray source and a fixed detector array. By altering the speed at which the x-ray source is rotated through a plurality of projection angles, the angular spacing of the samples is altered. Accordingly, the spirit and scope of the invention are to be limited only by the terms of the appended claims.

What is claimed is:

1. A method for generating an image of an object using an imaging system, the imaging system including an x-ray detector array and a rotating x-ray source, the x-ray source projecting an x-ray beam toward the detector array along a projection angle, said method comprising the steps of:

rotating the x-ray source through a plurality of projection angles;

collecting a plurality of samples projection data; and altering an angular spacing between each projection data sample as a function of the projection angle.

2. A method in accordance with claim 1 further comprising the step of generating a volumetric tomographic image of the entire object utilizing the projection data.

3. A method in accordance with claim 1 wherein the detector array is a digital detector panel.

4. A method in accordance with claim 1 wherein altering an angular spacing between each projection data sample as a function of the projection angle comprises the step of altering a rotational speed of the x-ray source.

5. A method in accordance with claim 1 wherein altering an angular spacing between each projection data sample as a function of the projection angle comprises the step of altering a sampling frequency of the detector array.

6. A method in accordance with claim 1 wherein altering an angular spacing between each projection data sample as a function of the projection angle comprises the steps of:

identifying a first projection angle range; and identifying a second projection angle range.

7. A method in accordance with claim 6 wherein altering an angular spacing between each projection data sample further comprises the steps of:

rotating the x-ray source at a first speed for the first projection angle range; and rotating the x-ray source at a second speed for the second projection angle range.

8. A method in accordance with claim 6 wherein the object includes at least one high density element having a sharp structure, wherein identifying a first projection angle region comprises the steps of:

determining a sharp structure axis; and selecting a center of the first projection angle range to be approximately aligned along the sharp structure axis.

9. A method in accordance with claim 8 wherein the object high density element sharp structure axis is aligned with a patient y-axis, and wherein selecting a center of the first projection angle range to be approximately aligned along the sharp structure axis comprises the step of selecting a center of the first projection angle range to be approximately aligned with the patient y-axis.

10. A method in accordance with claim 6 wherein identifying a second projection angle comprises the step of identifying a second projection angle region center in accordance with:

$$C_{SPAR} = 180 \text{ degrees} + C_{FPAR};$$

where:

$C_{SPAR}$ = the second projection angle region center; and $C_{FPAR}$ = a first projection angle region center.

11. A method in accordance with claim 6 wherein further comprising the step of applying a weighting function to the collected projection data.

12. A method in accordance with claim 11 wherein applying weighting function to the projection data comprising the steps of:

applying a first weight to the projection data collected from the first projection angle range; and applying a second weight to the projection data collected from the second projection angle range.

13. A method in accordance with claim 12 wherein the first weight is less than the second weight.

14. A method in accordance with claim 6 wherein the identifying a first projection angle range comprises the steps of:

determining a starting angle; and selecting a center of the first projection angle range to be approximately aligned along the starting angle.

15. A method in accordance with claim 1 wherein collecting a plurality of samples of projection data comprises the step of interpolating the samples of projection data.

16. An imaging system for generating an image of an object, said imaging system comprising an x-ray detector array and a rotating x-ray source, said x-ray source projecting an x-ray beam toward said detector array along a projection angle, said system configured to:

rotate said x-ray source through a plurality of projection angles;

collect a plurality of samples projection data; and alter an angular spacing between each projection data sample as a function of the projection angle.

17. An imaging system in accordance with claim 16 further configured to generate a volumetric tomographic image of the entire object utilizing the projection data.

18. An imaging system in accordance with claim 16 wherein said detector array comprises a digital detector panel.

19. An imaging system in accordance with claim 18 wherein said detector array is approximately 40 cm by approximately 40 cm.

20. An imaging system in accordance with claim 16 wherein to alter an angular spacing between each projection data sample as a function of the projection angle, said system configured to alter a rotational speed of said x-ray source.

21. An imaging system in accordance with claim 16 wherein to alter an angular spacing between each projection data sample as a function of the projection angle, said system configured to alter a sampling frequency of said detector array.

22. An imaging system in accordance with claim 16 wherein to alter an angular spacing between each projection data sample as a function of the projection angle, said system configured to:

identify a first projection angle range; and identify a second projection angle range.

23. An imaging system in accordance with claim 22 wherein to alter an angular spacing between each projection data sample, said system further configured to:

rotate said x-ray source at a first speed for said first projection angle range; and rotate said x-ray source at a second speed for said second projection angle range.

24. An imaging system in accordance with claim 22 wherein the object includes at least one high density element having a sharp structure, wherein to identify a first projection angle region, said system configured to:

determine a sharp structure axis; and select a center of the first projection angle range to be approximately aligned along the sharp structure axis.

25. An imaging system in accordance with claim 24 wherein the sharp structure axis is aligned with a patient y-axis, and wherein to select a center of the first projection angle range to be approximately aligned along the sharp structure axis, said system configured to select a center of the first projection angle range to be approximately aligned with the patient y-axis.

26. An imaging system in accordance with claim 22 wherein to identify a second projection angle, said system configured to identify a second projection angle region center in accordance with:

$$C_{SPAR} = 180 \text{ degrees} + C_{FPAR};$$

where:

$C_{SPAR}$ = the second projection angle region center; and $C_{FPAR}$ = a first projection angle region center.

27. An imaging system in accordance with claim 22 wherein said system further configured to apply a weighting function to the collected projection data.

28. An imaging system in accordance with claim 27 wherein to apply a weighting function to the projection data, said system configured to:

apply a first weight to the projection data collected from said first projection angle range; and apply a second weight to the projection data collected from said second projection angle range.

29. An imaging system in accordance with claim 28 wherein said first weight is less than said second weight.

30. An imaging system in accordance with claim 22 wherein to identify a first projection angle range, said system configured to:

determine a starting angle; and select a center of the first projection angle range to be approximately aligned along said starting angle.

31. An imaging system in accordance with claim 22 wherein to collect a plurality of samples of projection data, said system configured to interpolate said samples of projection data.

* * * * *